United States Patent [19]
Bergeron et al.

[11] Patent Number: 6,068,851
[45] Date of Patent: May 30, 2000

[54] FORMULATION FOR USE IN THE PREVENTION OF PATHOGEN INDUCED DISEASES INCLUDING HIV AND HSV

[75] Inventors: Michel G. Bergeron, Sillery; André Désormeaux; Michel Tremblay, both of Neufchatel, all of Canada

[73] Assignee: Infectio Recherche, Inc., Sainte Foy, Canada

[21] Appl. No.: 09/051,300

[22] PCT Filed: May 9, 1997

[86] PCT No.: PCT/CA97/00319

§ 371 Date: Jan. 13, 1999

§ 102(e) Date: Jan. 13, 1999

[87] PCT Pub. No.: WO97/42962

PCT Pub. Date: Nov. 20, 1997

Related U.S. Application Data

[60] Provisional application No. 60/017,106, May 9, 1996.

[51] Int. Cl.[7] ................................................ A61F 2/00
[52] U.S. Cl. ................ 424/424; 424/422; 424/427; 424/430; 424/432; 424/433; 424/434; 424/435; 424/436; 424/450; 424/486; 424/78.06; 424/78.07; 514/45; 514/46; 514/47
[58] Field of Search ...................... 424/422, 424, 424/427, 430, 432, 433, 434, 435, 436, 450, 484, 486, 78.02, 78.06, 78.07; 514/45, 46, 47

[56] References Cited

U.S. PATENT DOCUMENTS

| | | | |
|---|---|---|---|
| 5,151,438 | 9/1992 | Sham et al. | 514/357 |
| 5,292,516 | 3/1994 | Viegas et al. | 424/423 |

FOREIGN PATENT DOCUMENTS

| | | |
|---|---|---|
| 0 525 655 A1 | 2/1993 | European Pat. Off. . |
| 2 660 192 | 10/1991 | France . |
| WO 94/03157 | 2/1994 | WIPO . |
| WO 95/10268 | 4/1995 | WIPO . |

*Primary Examiner*—Jeffrey Stucker
*Attorney, Agent, or Firm*—Godfrey & Kahn, S.C.

[57] ABSTRACT

This invention relates to formulations comprising film-forming components capable of forming per se a physical barrier to pathogens. Thermoreversible gels such as poloxamers are particularly preferred for that use. The film-forming formulations may further comprise microbicides, spermicides or any other drug, which choice is guided by the pathogen, organism or the disease to be inactivated or treated. The formulations are therefore efficient as a physical, and optionally, as a chemical or pharmacological barrier as well as usable as a sustained drug-release system at the locus of administration. A part of the drug may also be entrapped in liposomes or other drug carriers. These formulations are intended for use in the prevention of sexually transmitted diseases, as well as in the treatment of infections, cancer, inflammation or any disease or state which requires a pharmacological treatment. Formulations are applicable to mucosae, skin and eye, for example.

42 Claims, 9 Drawing Sheets

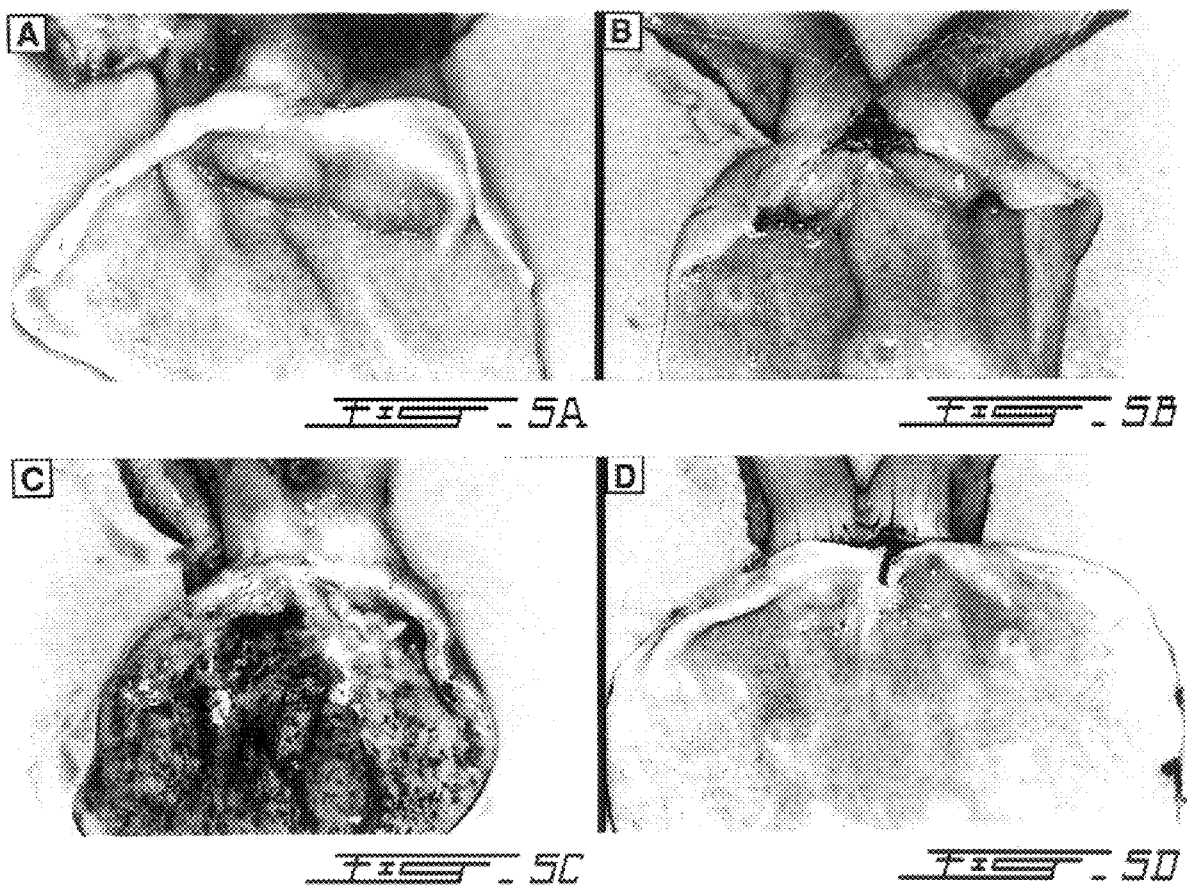

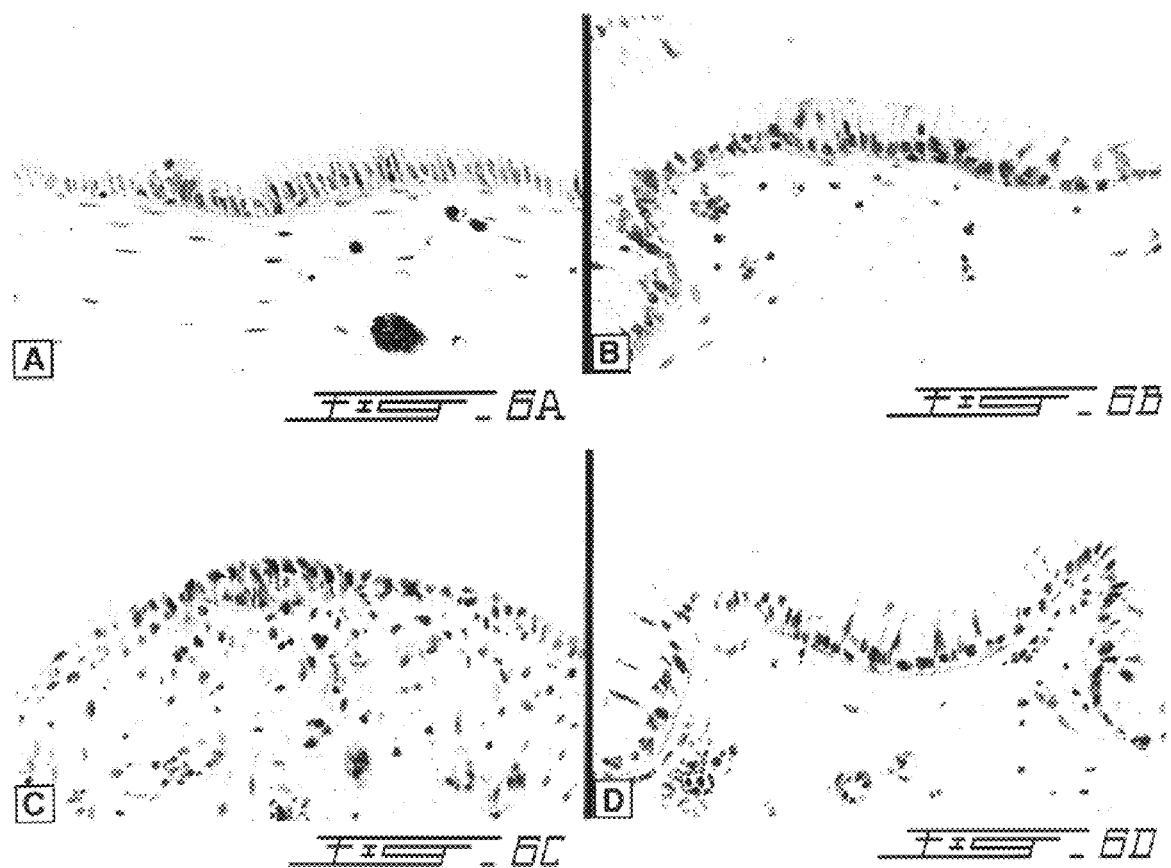

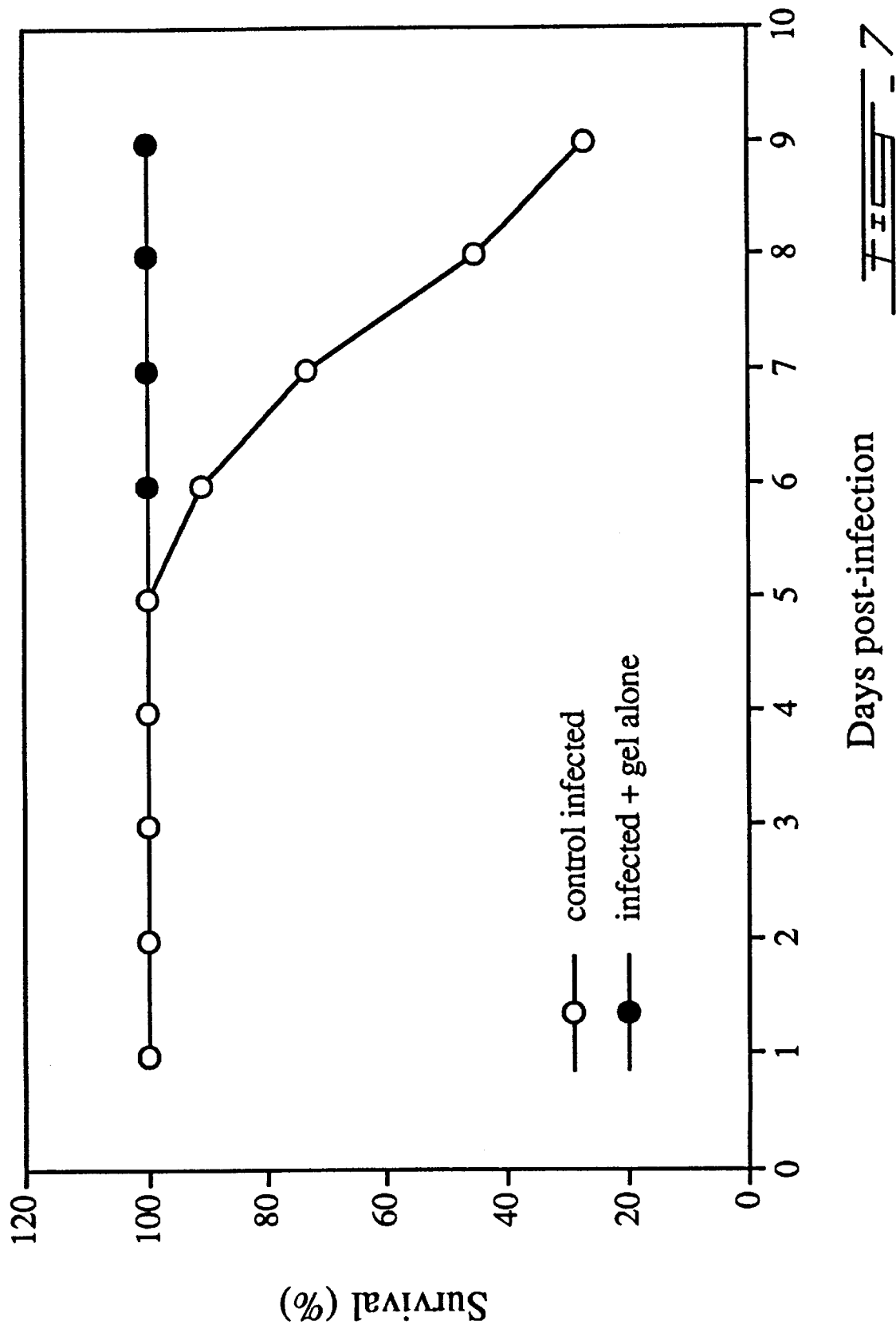

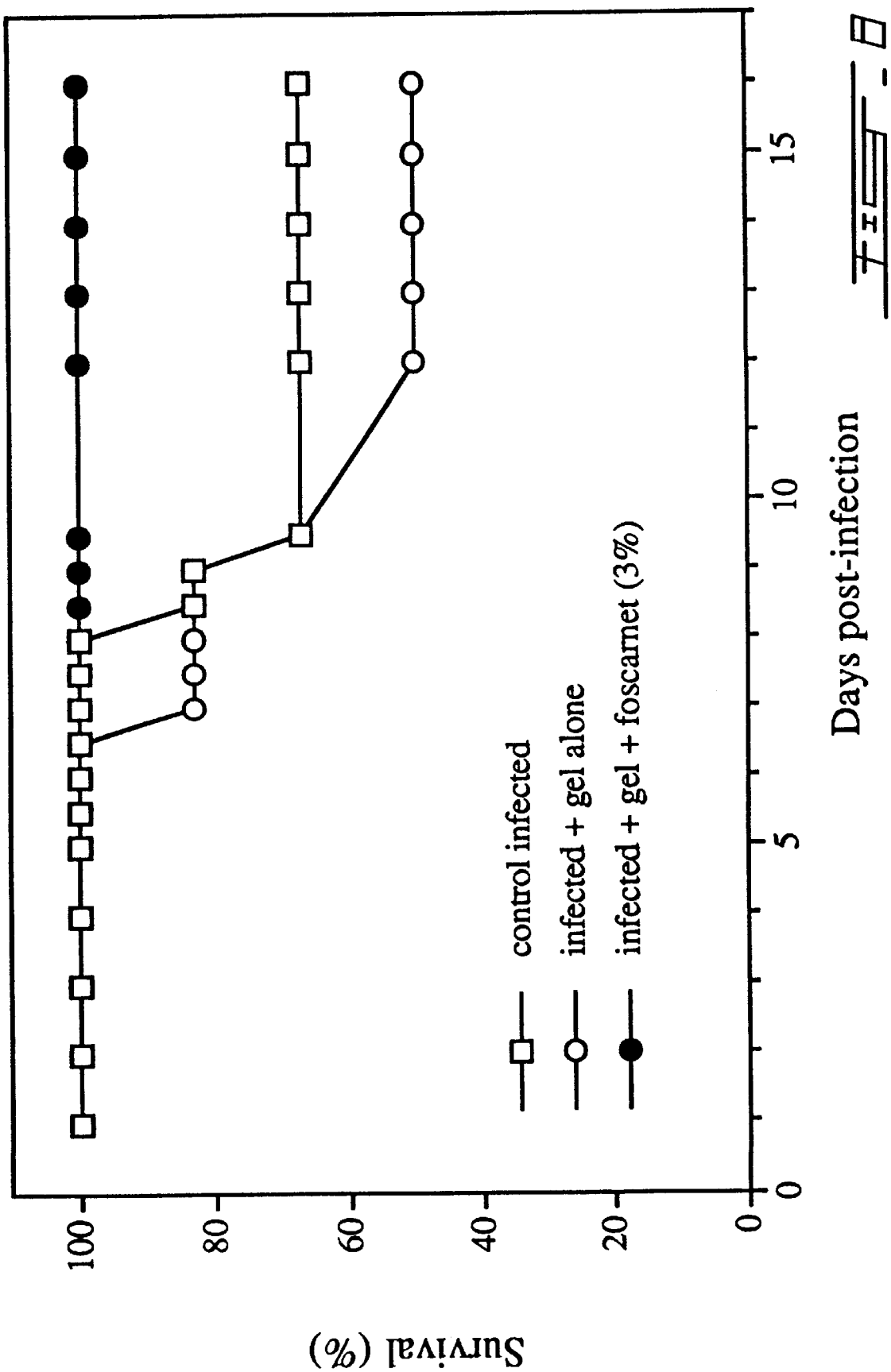

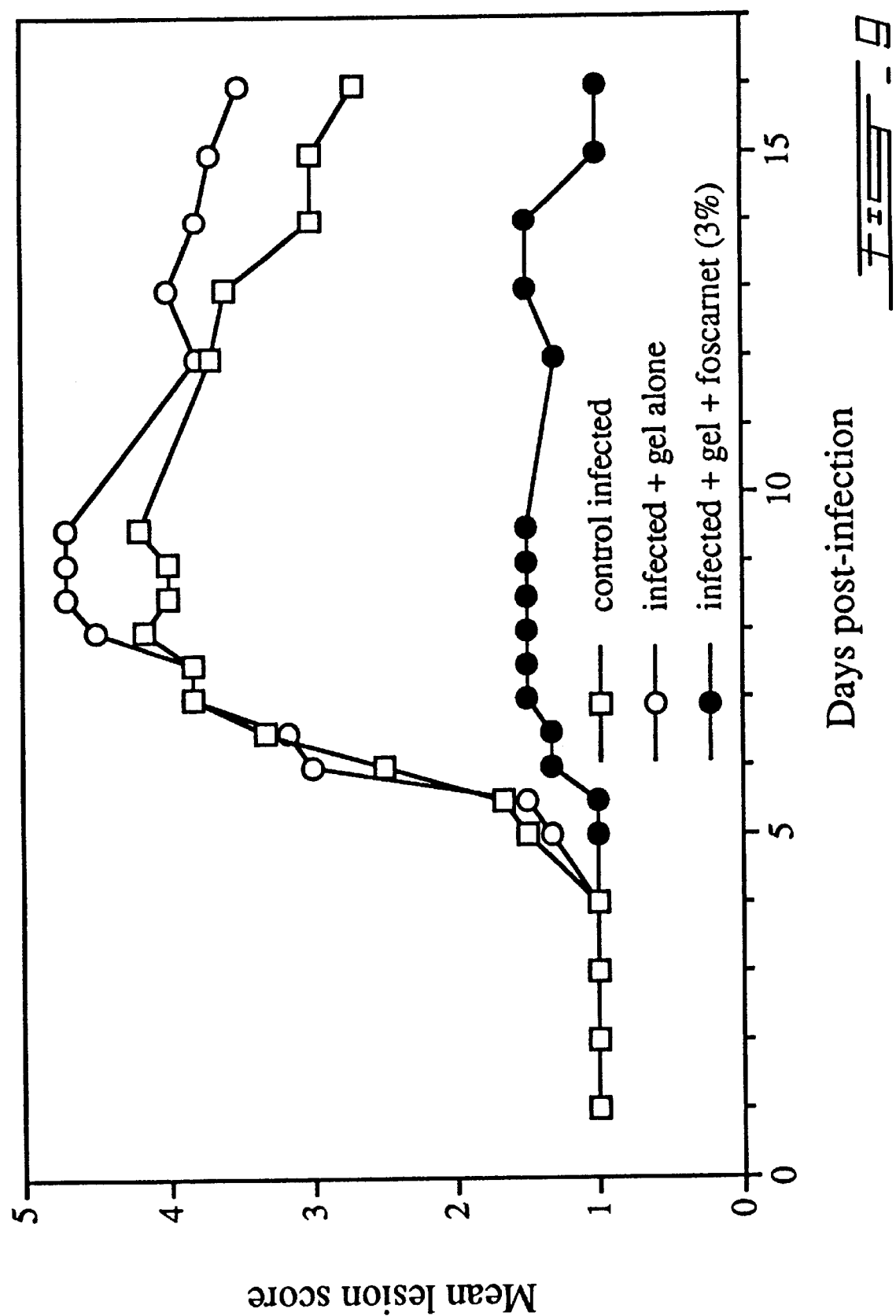

FORMULATION FOR USE IN THE PREVENTION OF PATHOGEN INDUCED DISEASES INCLUDING HIV AND HSV

This application is continuation of U.S. provisional application 60/017,106 filed May 9, 1996 and the national phase of PCT/CA97/00319 filed May 9, 1997.

FIELD OF THE INVENTION

This invention relates to formulations comprising film-forming components, particularly to topical formulations, and more particularly to topical formulations i) to prevent the transmission of pathogens through mucosae and/or skin, more particularly those useful to prevent the sexual transmission of human immunodeficiency virus and other sexually transmitted diseases, ii) to treat lesions of mucosae and/or skin caused by pathogens or any other disease and iii) to prevent and/or treat any other pathogen of mucosae and/or skin including any infection, cancer, inflammatory process or any other disease.

BACKGROUND OF THE INVENTION

As there is no truly effective treatment or vaccine against AIDS, preventive measures are the only tools that can presently reduce the transmission of human immunodeficiency virus (HIV). The consistent and careful use of appropriate condoms represents an effective barrier to prevent HIV transmission. However, condoms should be used for almost all sexual intercourses to significantly reduce the probability of acquiring infection. In Africa, the most intensive prevention programs were only able to increase condom use to approximately 70% of all sexual intercourses in female prostitutes. Thus, doubts arise about the possibilities of condom promotion in controlling the AIDS epidemic in high risk groups. In situations where heterosexual transmission of HIV is important, preventive measures that depend on female behaviour would be an additional tool to control the epidemic. Since the women's compliance to preventive interventions for sexually transmitted diseases (STDs) is superior to that of men, regular use of such a preventive measure may be possible. This is reinforced by the fact that the introduction of different products into the vagina is a common practice in developing countries. Such a protective tool may also be useful in male homosexual relations as it could provide additional protection under the control of the receptive partner.

The development of microbicides to prevent the sexual transmission of HIV in humans constitutes actually one of the most important research areas in the field of HIV prevention. One of the major difficulties with this approach is that drugs used to control HIV transmission, including spermicides such as nonoxynol-9, have been shown to induce local inflammation and ulcerations which might favour the entry of HIV. As the number of individuals infected with HIV is growing dramatically throughout the world, there is an urgent need to develop active products and/or vehicles that could reduce the transmission of HIV with minimal mucosal irritation and minimal effects on the vaginal flora and pH. The use of gel formulations of microbicides or any other drug, that could be topically applied to the vaginal, cervical and/or ano-rectal mucosae of humans, represents a convenient strategy to achieve such a goal. The microbicides or any other drug can be entrapped into the gel formulations either as free or encapsulated into drug carriers such as liposomes, nanoparticles or cyclodextrins. Such microbicidal gels could prolong the local microbicidal activity, eliminate local irritation and reduce systemic side effects of incorporated active agents.

Herpes simplex virus type 2 (HSV-2) is one of the most common STDs. An animal model of intravaginal HSV-2 infection represents an interesting approach to evaluate the efficacy of our gel formulations to prevent the sexual transmission of that pathogen. Another important herpes virus infection is herpes simplex virus type 1 (HSV-1) which is a neurotropic virus that infects principally the neuroectodermal tissues including the skin, the peripheral nerves and the central nervous system. Recurrent HSV-1 cutaneous infections are frequently observed in immunocompromised patients. Zoster is clinically characterized by an unilateral dermatome distribution and by the occurrence of neuralgic pain both as a result of peripheral nerve involvement. Although, it is a mild disease, cutaneous HSV infections can be troublesome, especially for patients with frequent episodes. Foscarnet and acyclovir are both antiviral agents active against all types of herpes viruses. However, the currently available treatments, either topical or systemic, have only a limited efficacy particularly for the treatment of symptomatic recurrent herpes. Therefore, there is a need to develop new topical formulations of antiviral agents which could improve the efficacy of drugs.

Liposomes are microscopic vesicles composed of one or several lipid bilayers separated by aqueous compartments in which a variety of drugs can be incorporated. Numerous studies have shown an improved therapeutic index and a reduced toxicity for drugs entrapped in liposomes. We have already demonstrated that the encapsulation of anti-HIV agents into liposomes allows high cellular penetration, good in vitro antiviral activity against HIV, efficient targeting of macrophage-rich tissues and a marked improvement of the pharmacokinetics of drugs (Desormeaux et al., 1994, AIDS 8:1545–1553; Makabi-Panzu et al., 1994, AIDS Res. Hum. Retroviruses 10:1463–1470; Dusserre et al., 1995, AIDS 9:833–841; Harvie et al., 1995, AIDS 9:701–707; Harvie et al., 1996, Antimicrob. Agents Chemother. 40:225–229). To our knowledge, liposome-encapsulated drugs have never been used to prevent the mucosal transmission of infectious agents. When applied locally to mucosa or skin, liposomes are usually taken up by monocytes and macrophages and also by Langerhans cells which may capture and harbor HIV. Consequently, in contrast with free drugs, which tend to diffuse rapidly through the mucosa and reach the circulation, the use of drugs within liposomes and incorporated into a gel formulation should concentrate the active agents within infected cells as well as within cells susceptible to HIV infection. Such drug delivery system is even more attractive as it was shown that liposomes are very well tolerated when given topically (Parnham and Wetzig, 1993, Chem. Phys. Lipids 64:263–274).

U.S. Pat. No. 5,292,516 describes gel formulations comprising poloxamers which are used as drug delivery systems. However, no mention is made in that reference that the gels themselves are physical barriers per se impeding permeation of pathogens therethrough.

The international patent publication WO 95/10268 describes a composition comprising poloxamer 407 gel (18% w/w) containing cysteamine to prevent HIV infection. This reference indeed teaches that poloxamer 407 gel can be used as a vaginal gel, but it does not suggest that the poloxamer itself might be used as a physical barrier to prevent the transmission of a pathogen and its permeation through the membrane of mucosa. Furthermore, this reference does not teach that the gel formulation could act as a pharmacological barrier to prevent the infection of host cells. In addition, this reference does not show any in vitro and in vivo evidence that the gel formulation might be efficient to prevent the transmission of pathogens.

There is, therefore, still a need for a method and compositions for preventing transmission of pathogens through the membrane of mucosae and/or skin which compositions and method would result in the creation of a physical barrier to permeation of pathogens, and optionally in the further creation of a chemical or pharmacological barrier to pathogen transmission.

SUMMARY OF THE INVENTION

It is an object of the present invention to provide a method i) to prevent the transmission of pathogens through mucosae and/or skin, more particularly those useful to prevent the sexual transmission of human immunodeficiency virus and other sexually transmitted diseases, ii) to treat lesions of mucosae and/or skin caused by pathogens or any other disease and iii) to prevent and/or treat any other pathogen of mucosae and/or skin including any infection, cancer, inflammatory process or any other disease.

It is an object of the present invention to provide formulations to prevent the transmission of pathogens through mucosae and/or skin, more particularly those useful to prevent the sexual transmission of human immunodeficiency virus and other sexually transmitted diseases. It is another object of the present invention to provide formulations to treat lesions of the mucosae and/or skin. It is still another object of the invention to provide formulations to prevent and/or treat any other pathogen of mucosae and/or skin including any infection, cancer, inflammatory process or any other disease.

In preferred embodiments, the above method and formulations are effective to prevent the transmission of STDs, more particularly HIV, by acting as a physical, chemical and/or pharmacological barrier. The physical barrier comprises a film-forming component which is applied to the surface of mucosa or skin, preferably in the form of gel, cream or ointment. Most preferably, a thermoreversible gel is applied in a liquid form, spreads on this surface and forms a semi-solid coating after it reaches the temperature of this body surface. In a more preferred embodiment, the thermoreversible gel is composed of poloxamer 407. Similar polymers like poloxamines can also be used. The semi-solid gel alone acts as a mechanical (physical) barrier which blocks access of either free or intracellular pathogen to the mucosa or skin. The chemical and/or pharmacological barrier comprises a microbicide, a spermicide and/or any other drug. For the purpose of the invention, the term "microbicide" is intended to cover any agent effective against pathogens. A chemical barrier comprises free microbicide(s), spermicide (s) and/or any other drug entrapped in gel, which chemically destroys pathogens coming into contact with the mucosa or skin and also reduces or eliminates toxicity of the microbicides, spermicides and/or other drug to epithelial cells. Microbicides, spermicides and/or any other drug may be released from the gel or they may get in situ on pathogens or infected cells. In a more preferred embodiment, the chemical barrier is intended to be used in gel applicable on the vaginal, cervical and/or ano-rectal mucosae, and is a compound such as nonoxynol-9. A pharmacological barrier may comprise a microbicide, a spermicide and/or any other drug effective against the pathogen such as an adsorption inhibitor which prevents pathogen's entry into a target cell, an inhibitor for an enzyme necessary for the replication of the pathogen or a metabolic poison for the pathogen. In a more preferred embodiment, the pharmacological barrier is intended to be used in gel applicable on the vaginal, cervical and/or ano-rectal mucosae to prevent the sexual transmission of HIV and comprises inhibitors of HIV protease and reverse transcriptase (alone or in combination). These inhibitors are preferably encapsulated within drug carriers such as liposomes, nanoparticles or cyclodextrins, which encapsulation results in the concentration of the inhibitors within the HIV target host cells, preventing either the production of infectious viral particles or infection of uninfected cells. If infected cells in sperm can reach the mucosa, the gel formulation of anti-HIV agents could prevent HIV infection of host cells, such as macrophages, lymphocytes, Langerhans and M cells.

In a preferred embodiment, the gel formulation is composed of poloxamer 407. In a more preferred embodiment, the poloxamer 407 concentration is 19.5% (w/w). In another preferred embodiment, the gel formulation is composed of poloxamer 407 (19.5% w/w) and contains nonoxynol-9 as microbicide. In another preferred embodiment, the gel formulation is composed of poloxamer 407 (19.5% w/w) and contains liposomes composed of distearoylphosphatidylcholine (DSPC): distearoylphosphatidylglycerol (DSPG) in a molar ratio of 10:3 within which 2'-3'-dideoxyinosine (ddi) is entrapped as antiviral drug. In another preferred embodiment, the gel formulation is composed of poloxamer 407 (19.5% w/w) and contains liposomes composed of DSPC: DSPG: distearoylphosphatidylethanolamine-polyethylene-glycol (DSPE-PEG) in a molar ratio of 10:3:1.45 within which ddI is entrapped as antiviral drug. In another preferred embodiment, the gel formulation is composed of poloxamer 407 (19.5% w/w) and contains liposomes composed of dipalmitoylphosphatidylcholine (DPPC):dicetylphosphate (DP): cholesterol (CHOL) in a molar ratio of 4:1:5 within which 2'-3'-dideoxycytidine (ddC) is entrapped as antiviral drug. Yet in another preferred embodiment, the gel formulation is composed of poloxamer 407 (19.5% w/w) and contains liposomes composed of DPPC:dipalmitoylphosphatidylglycerol (DPPG) in a molar ratio of 10:3 within which foscarnet is entrapped as antiviral drug.

In another more preferred embodiment, the gel formulation is composed of poloxamer 407 (18% w/w). In another preferred embodiment, the gel formulation is composed of poloxamer 407 (18% w/w) and contains foscarnet as a microbicide. In still another preferred embodiment, the gel formulation is composed of poloxamer 407 (18% w/w) and contains acyclovir as a microbicide. In still another preferred embodiment, the gel formulation is composed of poloxamer 407 (18% w/w) and contains liposomes composed of DPPC:DPPG in a molar ratio of 10:3 within which foscarnet is entrapped as antiviral drug. In still another preferred embodiment, the gel formulation is composed of poloxamer 407 (18% w/w) and contains liposomes composed of DPPC:DPPG in a molar ratio of 10:3 within which acyclovir is entrapped as antiviral drug.

Concentrations of poloxamer may be varied upon conditions such as the liquid/gel transition temperature, the physical properties sought for the gel and the pH used in the making of the formulations.

The gel formulations are to be used for coating different types of mucosae such as vaginal, cervical, ano-rectal, eye, mouth, nose, or skin to prevent the penetration of pathogens such as viruses, bacteria, fungi, parasites, ectoparasites and mycoplasmas. Furthermore, the gel formulations can be injected into the eye for ophthalmic uses. The gel formulations can be combined with microbicides and/or antimicrobials and/or chemotherapeutic agents and/or antiinflammatory agents and/or any other drug and/or spermicides and/or liposomes (or other drug carriers). Furthermore, microbicides and/or spermicides can be combined with liposomes (or other drug carriers) to prevent or treat any disease of mucosae and/or skin. In addition, our gel and/or liposome (or other drug carriers) formulations can also be used as carriers of vaccines against infections caused by pathogens or any disease.

BRIEF DESCRIPTION OF THE DRAWINGS

FIG. 5 shows the effect of daily intravaginal application for two weeks of poloxamer gel (19.5% w/w) and/or nonoxynol-9 to rabbits.

FIG. 6 shows the corresponding histopathology of cervix after daily intravaginal application for two weeks of poloxamer gel (19.5% w/w) and/or nonoxynol-9 to rabbits.

FIG. 7 represents the efficacy of the poloxamer gel (19.5% w/w) to prevent the genital transmission of an Herpes simplex virus type 2 in mice.

FIG. 8 shows the efficacy of poloxamer gel alone (18% w/w) and of the gel containing 3% foscarnet to treat HSV-1 cutaneous lesions in mice.

FIG. 9 represents time evolution of the mean lesion score of HSV-1 infected mice without any treatment or treated with the poloxamer gel (18% w/w) alone or with the gel containing 3% foscarnet.

DETAILED DESCRIPTION OF THE INVENTION

Figure 1:
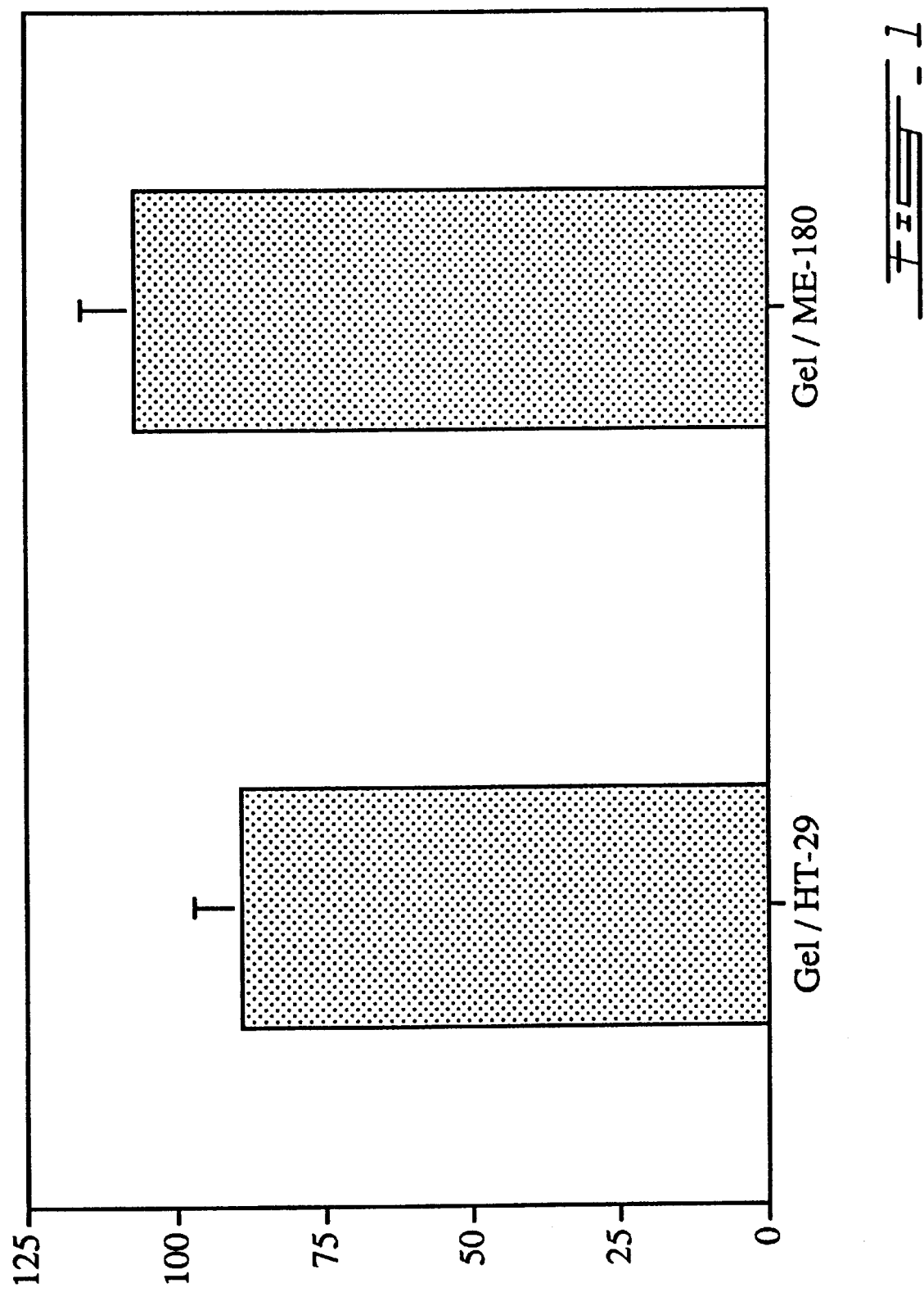
FIG. 1 shows the cytotoxicity of the poloxamer 407 gel (19.5% w/w) when applied to human cervical (ME-180) and colon (HT-29) epithelial cells.

The present invention is described herein below by way of specific examples and appended drawings, which purpose is to illustrate the invention rather than to limit its scope.
Gel Formulations Poloxamer 407 is a block copolymer of polyoxyethylene and polyoxypropylene in a 7:3 weight ratio with an average molecular weight of 12500. One important characteristic of this block copolymer is its ability to form a thermoreversible gel. The transition from the liquid state at low temperature to the gel state at body temperature (the phase transition temperature being dependent, in part, on the concentration of the gel and on the ionic strength) allows a number of interesting medical applications including topical applications. Such characteristic is of prime importance because when applied topically in their fluid state to the mucosa, the gel formulations will form an artificial barrier which could resist to biological fluids. Because of the extremely low toxicity and irritancy of our gel formulations, they represent an attractive approach for topical drug delivery systems. Details for the preparation of the gel formulations are provided in Example 1. This invention covers gel formulations of poloxamer 407 of any suitable concentration (w/w), and more particularly those between about 10 and 50% w/w. This invention also covers any other film-forming component, gel, cream, ointment or thermoreversible substance including other poloxamers, poloxamines or chemicals.
Microbicides, Spermicides and Other Drugs Any microbicide which is effective against pathogens (viruses, bacteria, fungi, parasites, ectoparasites and mycoplasmas) is under the scope of this invention. Particularly those which are effective against HIV, HSV or other microbial diseases, and more particularly sexually transmitted diseases are preferred. Included in this class are spermicides (such as nonoxynol-9, benzalkonium chloride and menfegol), inhibitors of HIV adsorption (such as dextran sulfate), inhibitors of HIV protease (such as saquinavir, indinavir and ritonavir), inhibitors of HIV reverse transcriptase (such as AZT, ddC, ddi, 3TC and foscarnet) and other antivirals (such as ribavirin, acyclovir and ganciclovir) and any antimicrobial agent including antibiotics, antifungals, antivirals, antiparasitics and chemotherapeutic agents, antiinflammatory agents, antitoxins, immunotherapeutic agents to control any disease of mucosae and/or skin. It is important to mention that microbicides and/or spermicides can be used alone or in combination with any other drug. This invention also covers any combination of gels and/or microbicides and/or spermicides.
Liposomes In liposome-based products, we already showed that, for targeting HIV infected tissues, it is necessary to use liposome bilayer characteristics which allow high efficiency of drug encapsulation as well as reduced leakage of entrapped drug to take advantage of the ability of liposomes to deliver high concentrations of drugs into cells. Based on previous studies performed in our laboratory, these requirements can be obtained by using liposomes composed of i) a mixture of diacylphosphatidylcholine and diacylphosphatidylglycerol (in a molar ratio ranging between 10:1 and 1:1) wherein the acyl chains are either saturated or unsaturated and have between 14 and 18 carbon atoms in length or ii) a mixture of diacylphosphatidylcholine:dicetylphosphate: cholesterol, wherein the acyl chains of phosphatidylcholine are either saturated or unsaturated and have between 14 and 18 carbon atoms in length. However, it is deemed that a family of liposomal formulations can be easily derived therefrom, without affecting the valuable properties thereof. Therefore, this family of compounds comprises other acyl chains of given phospholipid formulations that have been tested in the practice.

The liposomes of the present invention also include sterically stabilized liposomes, defined herein as, liposomes which are modified by the incorporation of polymers, such as poloxamers and poloxamines, or of amphipathic lipids derivatized with a polymer, such as DSPE-PEG or dioleoylphosphatidylethanolamine-PEG (DOPE-PEG), or of any molecule which prolong the circulation time of liposomes. The liposomes of the present invention also include immunoliposomes, defined herein as, liposomes which are modified by the coupling of antibody molecules which enhance the targeting of specific cells. The liposomes of the present invention also include pH-sensitive liposomes, heat-sensitive liposomes, target-sensitive liposomes and any other types of liposomes that could be used for this purpose. This invention also covers any combination of gels and/or microbicides and/or spermicides and/or any other drug and/or liposomes and/or vaccines.

The preparation of liposomes in the present invention can be done by a variety of techniques such as those described in the literature (e.g. Szoka and Papahadjopoulos, 1980, Ann. Rev. Biophys. Bioeng. 9:467–508; Nassander et al., 1990, Liposomes in biodegradable polymers as drug delivery systems. p.261–338). Formulations of liposomes of the present invention include those having a mean particle diameter of any size prepared with any drug/lipid molar ratio. Incorporation of drugs into liposomes can be achieved by one or more methods of active and/or passive loading such as those described in the literature (e.g. Mayer et al., 1986, Chem. Phys. Lipids 40:333–345).

The following examples are intended to demonstrate the preparation of gel formulations that could be very efficient for the prevention of the sexual transmission of HIV and for the treatment of cutaneous lesions caused by herpes virus infections, but are in no way intended to limit the scope thereof. Our gel formulations could be applied to prevent the transmission of several other sexually transmitted diseases such as those due to viruses (herpes simplex virus, human papillomavirus, human immunodeficiency virus, *Molluscum contagiosum*, cytomégalovirus, Epstein-Barr virus, hepatitis A, B, C and), bacteria (*Neisseria gonorrhoeae, Treponema pallidum, Chlamydia trachomatis, Gardnerella vaginalis, Calymmatobacterium granulomatis, Haemophilus ducreyi, Streptococcus pyogenes, Helicobacter jejuni, Prevotella bivius*, enterococcus spp., peptococcus spp., Bacteroides spp., *Mobiluncus, enterobacteriaceae*, such as Shigella spp., Salmonella spp. and *Pseudomonas aeruginosa*), mycoplasmas (*Mycoplasma hominis, Ureaplasma urealyticum, Mycoplasma genitalium*), parasites (*Trichomonas vaginalis, Entamoeba histolytica*, Cryptospodirium, *Enterobius vermicularis, Giardia lamblia*, Mobiluncus), fungi (*Candida albicans*, Candida spp., *Torulopsis glabrata*, Dermatophytes) and ectoparasites (*Phthirus pubis, Pediculus humanus, Pediculus capitis, Sarcoptes scabiei*. In addition, the microbicidal gels could also be applied to the skin of health professionals who may get accidentally exposed to HIV or any other pathogen. Beside prevention of the transmission of infections, they may be used to treat these infections and to prevent or cure any pathology of mucosae and/or skin including cancer, inflammatory process or any other disease process.

Even though the description of this invention is limited to specific cases, any film-forming component and/or microbicide and/or spermicide and/or any other drug and/or liposomes (or other drug carriers) or any combination of the above are considered as potential candidates for the development of these topical presentations and are under the scope of this invention. The formulations also include any film-forming component and/or microbicide and/or spermicide and/or any other drug and/or liposomes (or other drug carriers) or any combination of these products at any suitable concentration.

EXAMPLE 1
Preparation of the Microbicidal Gels

The thermoreversible gels are prepared by adding an appropriate volume of distilled water, acetate buffer (0.2 M, pH 4.6), phosphate buffer (0.2 M, pH 6), HEPES buffer (0.02 M, pH 7.2) or any other suitable aqueous solution to the poloxamer 407 to obtain the desired ratio (w/w). The solution is then stirred at 4° C. to ensure complete dissolution and is let stand to allow stabilization of the gel matrix. An appropriate amount of microbicides, either as free or entrapped into drug carriers, are then added to the cold polymer solution.

EXAMPLES INVOLVING OUR GEL FORMULATIONS

For the purpose of testing the in vitro toxicity of our gel formulations on cell lines, the solutions were prepared with a pH near neutrality, to be compatible with the conditions wherein cell lines are viable. The pH can be adjusted to meet the requirements of each target tissue to be coated with the present formulations. For instance, if a formulation is to be used to coat vaginal mucosa, a slightly acidic pH will be used. The percentage of polymer may be adjusted accordingly to obtain an adequate transition temperature from liquid to solid state.

Drug Release Experiments

The poloxamer gel could act as a sustained-drug release system which prolong the local microbicidal activity of the incorporated active agents. We have studied the release of antiviral agents (AZT, ddC, ddi, foscarnet, acyclovir) from our poloxamer gel formulations using radiolabelled drugs and a diffusion cell made of two compartments separated by a dialysis membrane. Results showed that the release of drugs was increased at body temperature when compared to 4° C., although the viscosity of the gel is increased (data not shown). This is explained by the creation of large openings in the intermicellar network of the gel at high temperature which in turn increase the release of the incorporated active agents.

In vitro Toxicity Experiments

The cytotoxicity of the poloxamer 407 gel formulation (19.5% w/w) was evaluated in both human cervical (ME-180) and colon (HT-29) epithelial cells. Briefly, a semiconfluent monolayer of cells has been deposited on cell culture inserts in 24-well plates containing McCoy 5a medium and the gel was deposited on top of the cells. After an incubation of 24 hours, cells were washed with PBS to remove the gel and 500 µl of fresh medium with 50 µl of MTS solution (2 mg/ml in PBS) were added to each well. Plates were then incubated at 37° C. in a $CO_2$ incubator for 1 hour. The medium was then transferred into a 96-well plate and the optical density was read at 420 nm. Results showed that our gel formulation is non-cytotoxic when applied on the cell lines (FIG. 1).

Figure 2:
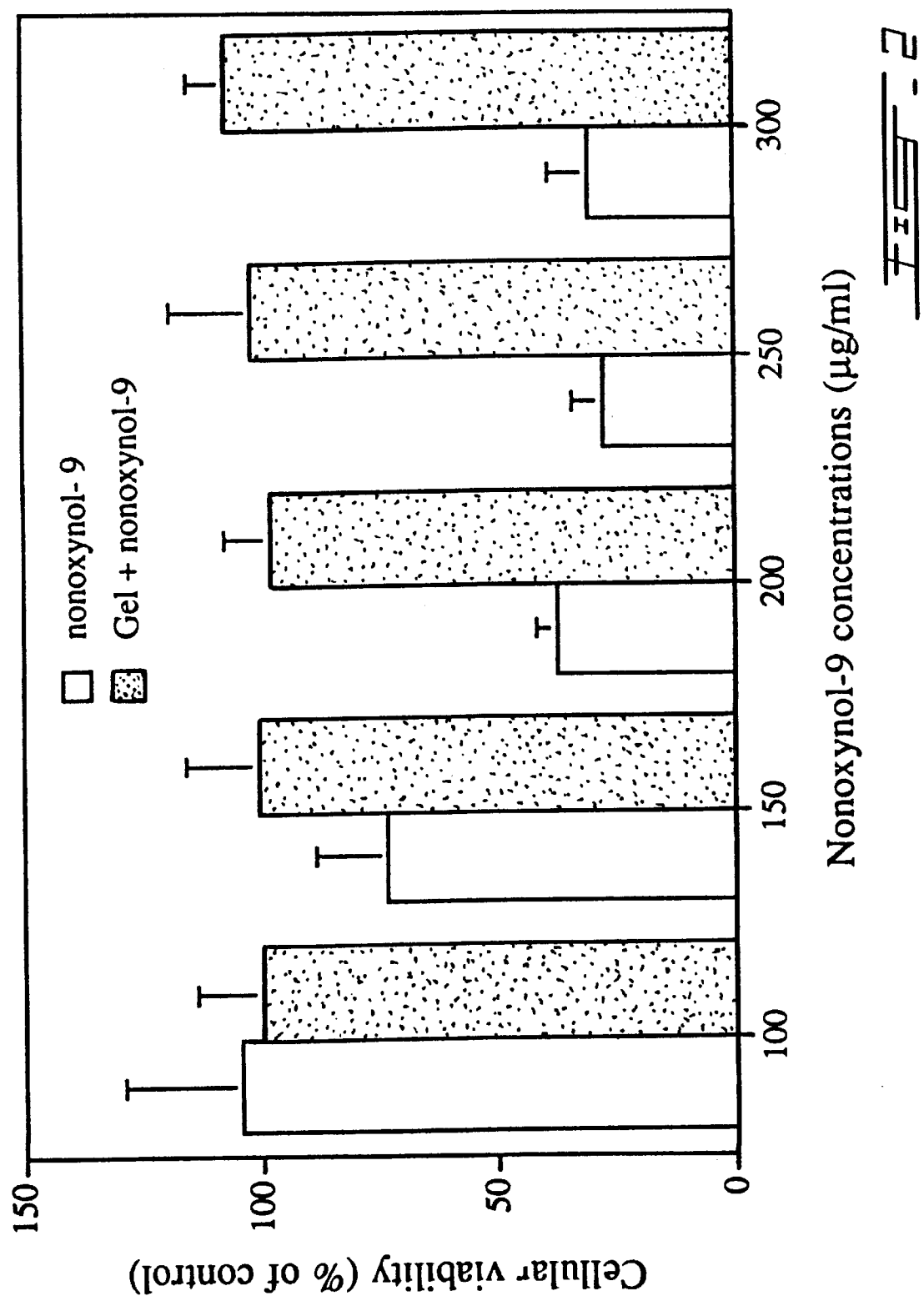
FIG. 2 represents the viability of human cervical cells following incubation with different concentrations of nonoxynol-9 either as free drug or incorporated into the poloxamer gel (19.5% w/w).

FIG. 2 shows the viability of human cervical cells following incubation with different concentrations of nonoxynol-9 either as free drug or incorporated into the poloxamer gel (19.5% w/w). As expected, nonoxynol-9 was highly toxic to the human cervical cells in a dose-dependent manner with a toxicity starting at 150 µg/ml. Of prime interest, we have demonstrated that the incorporation of that spermicide into our gel formulation was not toxic under the same experimental conditions.

Efficacy of the Gel as a Physical Barrier Against HIV

Figure 3:
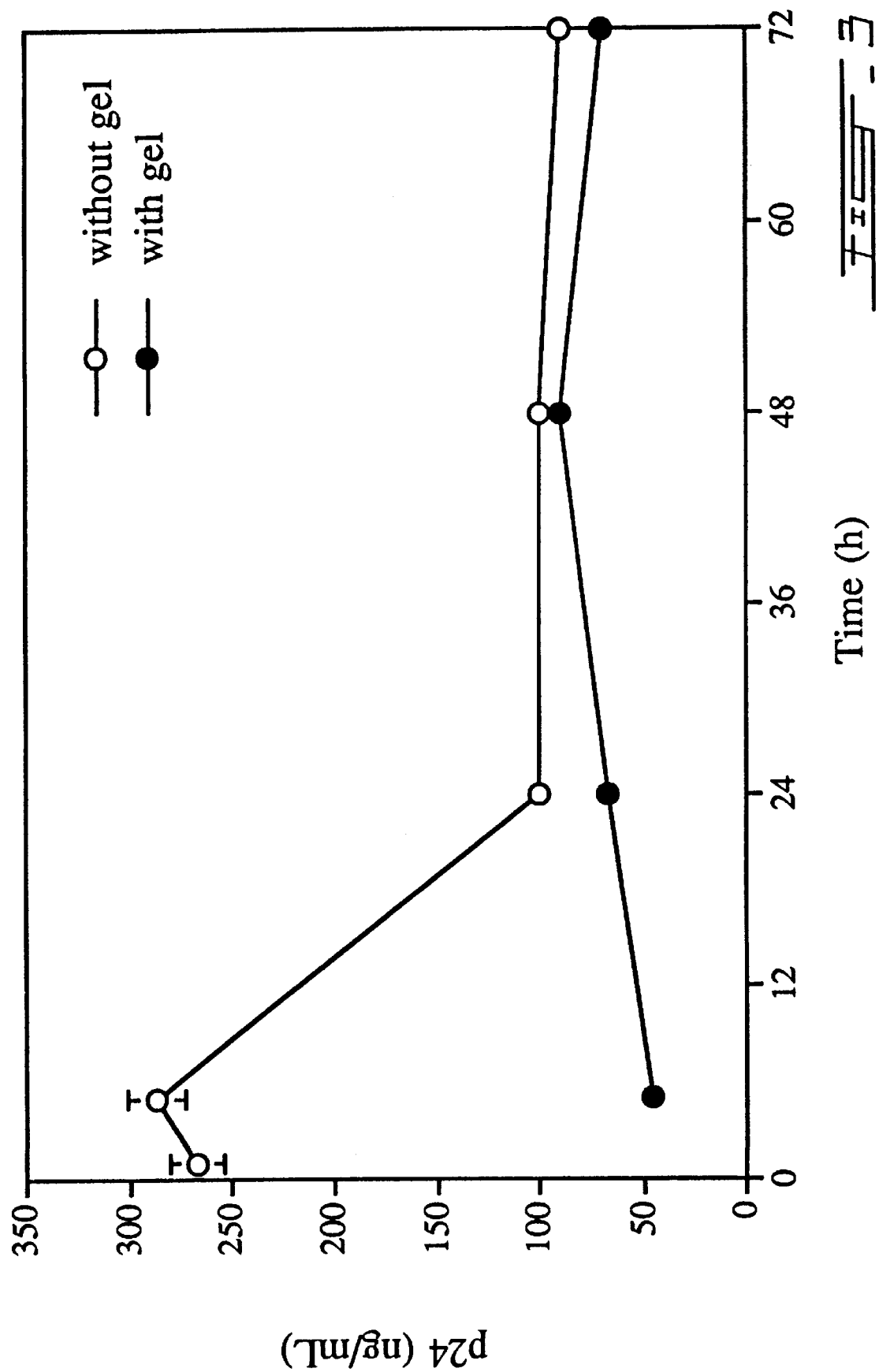
FIG. 3 represents the efficacy of the poloxamer 407 gel (19.5% w/w) as a physical barrier against HIV.

The ability of the poloxamer gel to block the passage of HIV-1 has also been monitored. In brief, cell culture inserts (0.4, um membrane pore size) were placed in 24-well plate. Thereafter, above the membrane, 100 µl of the gel (19.5% w/w in pH 7.2 HEPES buffer) was added prior to the addition of HIV-1IIIB (5000 pg of p24). Diffusion of viral particles through the gel and the membrane was evaluated over time by monitoring levels of p24 with a commercial enzymatic assay (Organon Teknika, Durham, N.C.). Results from this set of experiments indicate that the gel acts as a physical barrier to block the passage of HIV-1 particles by greatly reducing the amount of viral particles passing through the gel and membrane (FIG. 3).

Efficacy of the Gel to Prevent HIV Infection of T Cells

Figure 4:
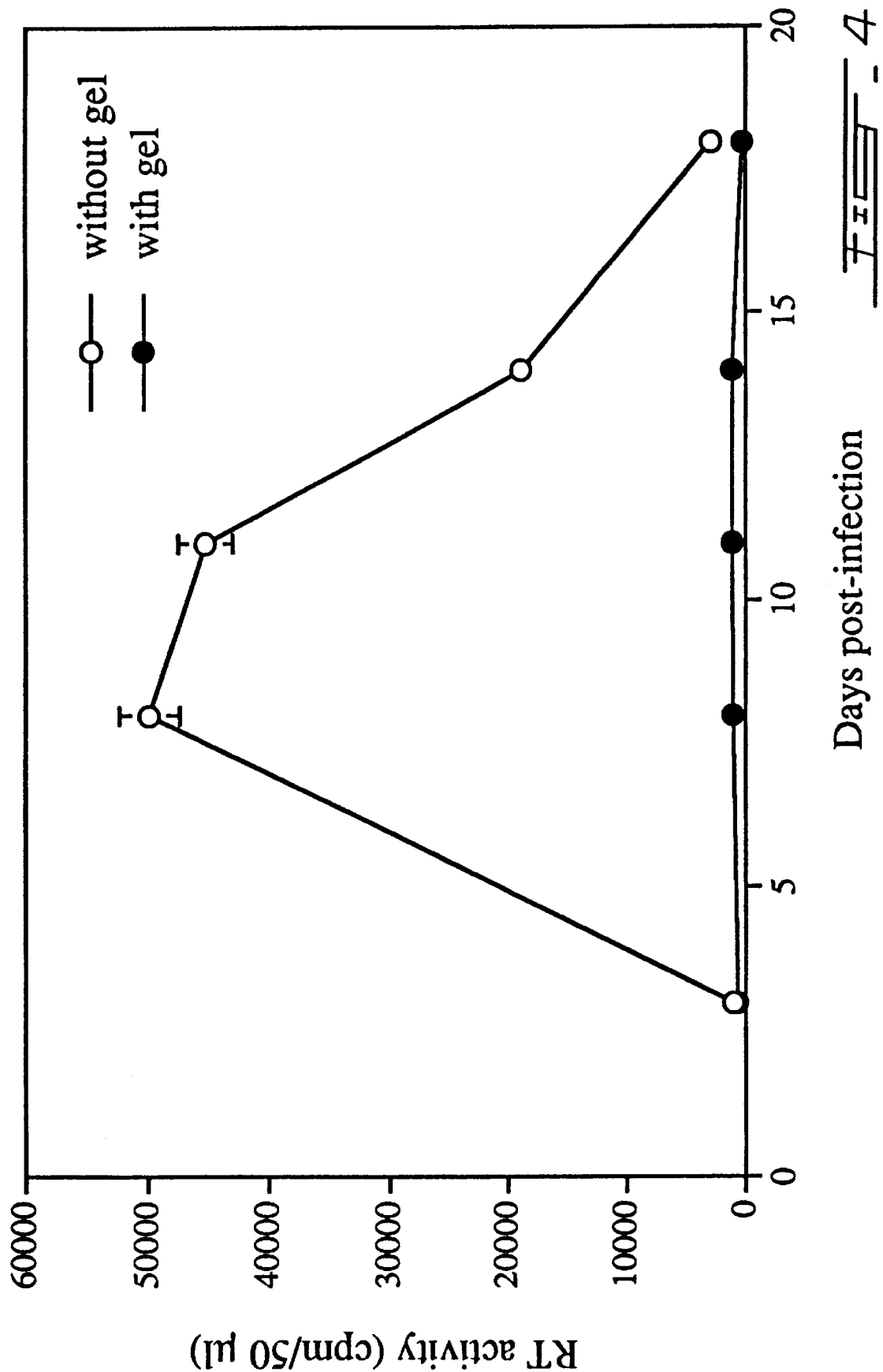
FIG. 4 shows the efficacy of the poloxamer 407 gel (19.5% w/w) to prevent infection of Sup-T1 cells with HIV.

Similar type of studies were carried out by adding at the bottom of each well an indicator cell line known to be highly susceptible to HIV-1 infection. The human CD4-positive T lymphoid cell line Sup-T1 was used for these experiments. Briefly, Sup-T1 cells were first seeded in 24-well plate ($1.25 \times 10^5$ cells/well). Next, cell culture inserts were placed in each well and, above the membrane, 100 μl of the gel (19.5% w/w in pH 7.2 HEPES buffer) was added prior to the addition of HIV-1IIIB (multiplicity of infection of 0.01; infectious viral particle per target cell). After 48 h of incubation at 37° C., inserts were removed and cells were washed to remove uninternalized viruses. Cells were maintained in complete culture medium and reverse transcriptase activity was determined in cell-free culture supernatants. As depicted in FIG. 4, virus replication is abolished by the presence of the gel. Results from the above experiments thereby suggest that the effect of the gel is either by physically blocking HIV particles and/or by negatively affecting viral infectivity. This experiment was repeated several times and gave similar results.

In vivo Toxicity Experiments

Studies have been performed to evaluate the tolerance and toxicity of the poloxamer 407 gel (19.5% w/w) when applied locally once daily for two weeks to the vaginal and cervical mucosae of New Zealand rabbits. The gel was applied in its fluid state to allow a good penetration into the irregularly shaped surfaces of the mucosae. Biopsies of the vaginal and cervical mucosae were performed on days 0, 4, 7 and 14 for histological examinations. FIG. 5 shows the effect of intravaginal application of gel and/or nonoxynol-9 on the vaginal and cervical mucosae of rabbits. Results showed that animals treated with the gel alone did not show signs of toxicity to vaginal and cervical mucosae (FIG. 5b) as compared to control (FIG. 5a). In contrast, nonoxynol-9 at a dose of 125 mg was very toxic as evidenced by the presence of epithelial disruption, irritation, necrosis and bleeding (FIG. 5c). Such toxicity induced by nonoxynol-9 might favour the entry of pathogens. However, the incorporation of nonoxynol-9 into the gel completely resolved the toxicity of the spermicide (FIG. 5d).

FIG. 6 shows the corresponding histopathology of cervix after intravaginal application once daily for two weeks of poloxamer gel (19.5% w/w) and/or nonoxynol-9. No major histology modifications was observed to the cervical mucosa of rabbits after the application of the gel alone (FIG. 6b) when compared to control (FIG. 6a). In contrast, optic microscopic examination of the cervical mucosa treated with nonoxynol-9 showed a large accumulation of eosinophiles in the sub-mucosa and induce a major loss of integrity of the epithelial cells (FIG. 6c). On the other hand, application of the same amount of spermicide incorporated into the gel showed no signs of toxicity (FIG. 6d) and was comparable to that observed with the gel alone.

In vivo Efficacy Experiments

The efficacy of the poloxamer gel (19.5% w/w) to prevent the genital transmission of HSV-2 was evaluated in mice. In brief, female Balb/c mice aged 4 weeks were used for this study. To increase susceptibility of mice to herpes, 2.5 mg of progesterone (Depo-Provera) was administered subcutaneously to each mouse 7 days prior to and on the day of inoculation with HSV-2. Anesthetized mice were inoculated with 10 μl of $2.4 \times 10^7$ pfu/ml of HSV-2 strain 333 after swabbing the vagina with a calcium alginate thin tipped swab premoistened with culture medium. To determine the efficacy of the poloxamer gel (19.5% w/w) to block the herpes infection, 10 μl of the gel was delivered with a pipette tip into the vagina a few minutes prior to the inoculation. The pipette tip was moved in and out four times to simulate stirring action of sexual intercourse while being cautious not to cause any bleeding. Four days post-infection, control infected animals demonstrated perineal oedema and redness and by 6 to 9 days, most of them died of encephalitis (FIG. 7). In contrast, no animal pretreated with the gel died (i.e. 100% survival) 9 days post-infection. These results clearly indicate that the use of our gel preparation could represent an innovative preventive measure to reduce the sexual transmission of STDs (including HIV).

The efficacy of poloxamer gel (18% w/w) alone and of the gel containing 3% foscarnet to treat HSV-1 cutaneous lesions in mice has also been investigated. In brief, hairless mice (SKH1, 35–42 days old) were anesthetized by intraperitoneal injection of a ketamine (70 mg/kg)/xylazine (11.5 mg/kg) solution. The virus (HSV-1, strain F; isolated from human facial vesicles; ATCC VR-733) was inoculated on the lateral side of the body in the lumbar skin area. The skin was scratched 6 times with a 27 gauge needle held vertically in a crossed hatched pattern. 50 μl of viral suspension ($1.5 \times 10^7$ pfu/ml was then applied onto the scratched skin area. The viral suspension was rubbed on the skin with a cotton tipped applicator saturated with the culture medium in which the virus was suspended. The scarified area was protected with a corn cushion (Schering Plough) which was maintained on the mice body with surgical tape. Mice develop vesicular cutaneous rash which rapidly coalesce to form a 4–5 mm wide band extending from the spine to the ventral midline of the affected dermatome similar to zoster-like infections. Virus spreads eventually to the central nervous system and causes encephalitis and ultimately death.

At 24 hours post-infection, mice were treated three times daily for 4 days with the gel alone or with the gel containing 3% foscarnet. Briefly, the surgical tape closing the aprture of the corn cushion was removed and the scarified skin area was cleaned using a cotton tipped applicator saturated with cold water. 15 μl of the gel with or without foscarnet was applied onto the scarified area. The aperture of the corn cushion was then closed again with surgical tape. Mice were examined twice daily for survival as well as for the evaluation of the lesion score according to the criteria presented in table 1.

TABLE 1

Criteria for scoring herpetic cutaneous lesions

| Score | Clinical manifestation |
|---|---|
| 0 | No sign of infection |
| 1 | Infection visible at the inoculation site only |
| 2 | Infection visible at the inoculation site along with swelling, crust and erythema |
|   | Infection visible at the inoculation site along with lesions forming away from inoculation site. Erythema in about half-body |
| 4 | Vesicular rash about half-body but not yet confluent |
| 5 | Vesicular rash totally confluent but not yet necrotic or ulcerated |
| 6 | Vesicular rash totally confluent but also necrotic or ulcerated. Hind limb paralysis, bloating and death |

FIG. 8 shows the survival of mice infected cutaneously with HSV-1, without any treatment, treated with the poloxamer gel (18% w/w) alone or with the gel containing 3% foscarnet. In untreated mice, the lethality of the infection was 33%. In mice treated with gel alone, we observed a mortality of 50% suggesting that the gel exert no therapeutic effect by itself in this herpes model. However, for mice treated with the poloxamer gel containing 3% foscarnet, all mice survived the infection demonstrating a good efficacy of the drug when incorporated into the gel.

FIG. 9 shows the time evolution of mean lesion score of mice infected cutaneously with HSV-1, without any treatment, treated with the poloxamer gel (18% w/w) alone and with the gel containing 3% foscarnet. In untreated mice, no pathological signs of cutaneous infection were visible during the first 4 days post-infection. On day 5, herpetic lesions began to appear in some mice in the form of small vesicles distant from the inoculation site. On day 6, almost all untreated mice developed herpetic skin lesions. Maximal mean lesion score was observed on day 8. Mean lesion score decreased on days 12 to 16 because of spontaneous regression of lesions in some mice. In mice treated with the gel alone, we observed a pattern largely similar to that seen with untreated mice suggesting that the gel alone has no therapeutic effect on the development of herpetic skin lesions. Of prime importance, we observed a marked reduction of mean lesion score in mice treated with the gel containing 3% foscarnet compared to untreated mice demonstrating a good efficacy of the drug incorporated into the gel. Therefore, the formulations properly performed drug delivery. Since they have also been shown to inhibit permeation of pathogens from an infected environment to a non-infected one (previous example with HSV-2), the present formulations have a dual purpose to act as drug delivery systems and as a barrier to contagion from external pathogens or to contagion from an infected subject to non-infected ones. Any adjuvant medication may be added to the formulations. For example, antihistaminics could be added to a formulation comprising a poloxamer and acyclovir when the intended use is for treating Herpes virus infections, where inhibition of itching and scratching is desirable to provide more comfort to the patient and to avoid spreading of infection.

This invention has been described hereinabove and it will be readily apparent to the skilled reader that variations could be brought to the embodiments described, without departing from the above teachings. These variations are under the scope of this invention, as defined in the appended claims.

What is claimed is:

1. A method for preventing the transmission of a pathogen through a person's skin or mucosa, which comprises the steps of:
   contacting the skin or mucosa with a gel component in a liquid state; and
   allowing the gel component to spread on the skin or mucosa;
   wherein, upon contact, the gel component solidifies to form a protective semi-solid layer effective to provide a physical barrier against passage of the pathogen through the skin or mucosa.

2. The method as set forth in claim 1, wherein the gel component further includes a biologically active ingredient.

3. The method as set forth in claim 2, wherein said biologically active ingredient comprises an agent effective against said pathogen.

4. The method as set forth in claim 3, which results into a physical barrier as well as an in situ chemical or pharmacological barrier against said pathogen.

5. The method as set forth in claim 1, wherein said person's mucosa is the vaginal or ano-rectal mucosae.

6. The method as set forth in claim 4, wherein said person's mucosa is the vaginal or ano-rectal mucosae.

7. The method as set forth in claim 3, wherein said biologically active ingredient comprises a microbicidal amount of microbicide.

8. The method as set forth in claim 7, wherein said microbicide is nonoxynol-9.

9. The method as set forth in claim 8, wherein the nonoxynol-9 is present in an amount of about 125 mg per dose unit.

10. The method as set forth in claim 2, which further results in protecting said person's skin or mucosa against local toxicity caused by said biologically active ingredient.

11. The method as set forth in claim 3, which further results in protecting said person's skin or mucosa against local toxicity caused by said biologically active ingredient.

12. The method as set forth in claim 7, which further results in protecting said person's skin or mucosa against local toxicity caused by said microbicide.

13. The method as set forth in claim 8, which further results in protecting said person's skin or mucosa against local toxicity caused by said nonoxynol-9.

14. The method as set forth in claim 1, wherein said pathogen is a virus.

15. The method as set forth in claim 3, wherein said pathogen is a virus.

16. The method as set forth in claim 4, wherein said pathogen is a virus.

17. The method as set forth in claim 7, wherein said pathogen is a virus.

18. The method as set forth in claim 9, wherein said pathogen is a virus.

19. The method as set forth in claim 13, wherein said pathogen is a virus.

20. The method as set forth in claim 3, wherein said biologically active ingredient is selected from the group consisting of saquinavir, indinavir, ritonavir, AZT, ddC, ddi, 3TC, foscarnet, ribavirin, acyclovir, and ganciclovir.

21. The method as set forth in claim 2, wherein said biologically active ingredient is encapsulated in liposomes, nanoparticles, or cyclodextrins.

22. The method as set forth in claim 3, wherein said biologically active ingredient is encapsulated in liposomes, nanoparticles, or cyclodextrins.

23. The method as set forth in claim 7, wherein said biologically active ingredient is encapsulated in liposomes, nanoparticles, or cyclodextrins.

24. The method as set forth in claim 20, wherein said biologically active ingredient is encapsulated in liposomes, nanoparticles, or cyclodextrins.

25. The method as set forth in claim 24, wherein the liposomes are composed of a mixture of diacylphosphatidylcholine:dicetylphosphate:cholesterol, and the acyl chains are either saturated or unsaturated, and have between 16–18 carbon atoms in length.

26. The method as set forth in claim 25, wherein the liposomes are composed of dipalmitoylphosphatidylcholine:dicetylphosphate:cholesterol in a molar ratio of 4:1:5, and the entrapped drug is ddC.

27. The method according to claim 24, wherein the liposomes are composed of a mixture of diacylphosphatidylcholine:diacylphosphatidylglycerol, wherein the acyl chains are either saturated or unsaturated, and have between 16–18 carbon atoms in length.

28. The method as set forth in claim 27, wherein the liposomes are composed of distearoylphosphatidylcholine:distearoylphosphatidylglycerol in a molar ratio of 10:3, and the entrapped drug is ddi.

29. The method as set forth in claim 27, wherein the liposomes are composed of distearoylphosphatidylcholine:distearoylphosphatidylglycerol: distearoylphosphatideylethanolamine-polyethyleneglycol in a molar ratio of 10:3:1.45, and the entrapped drug is ddi.

30. The method as set forth in claim 27, wherein the liposomes are composed of dipalmitoylphosphatidylcholine:dipalmitoylphosphatidylglycerol in a molar ratio of 10:3, and the entrapped drug is foscarnet.

31. The method as set forth in claim 1, wherein said gel component comprises a poloxamer.

32. The method as set forth in claim 31, wherein said poloxamer is poloxamer 407.

33. The method as set forth in claim 32, wherein said poloxamer is present in a concentration of about 10–50% (w/w).

34. The method as set forth in claim 32, wherein said poloxamer is present in a concentration of about 18 to 19.5% (w/w).

35. A barrier-forming composition, consisting essentially of a poloxamer and a buffer solution;

wherein, when applied to the surface of a person's skin or mucosa, the composition solidifies to form a protective semi-solid layer on the skin or mucosa, effective to provide a physical barrier against the passage of a pathogen through the skin or mucosa.

36. A barrier-forming composition as set forth in claim 35, wherein said poloxamer is poloxamer 407.

37. A barrier-forming composition, consisting essentially of a poloxamer, an effective amount of a microbicide, and a buffer solution;

wherein, when applied to the surface of a person's skin or mucosa, the composition solidifies to form a protective semi-solid layer on the skin or mucosa, effective to provide a physical barrier and a chemical barrier against a pathogen.

38. The barrier-forming composition as set forth in claim 37, wherein said poloxamer is poloxamer 407.

39. The barrier-forming composition as set forth in claim 37, wherein said microbicide is nonoxynol-9.

40. The barrier-forming composition as set forth in claim 38, wherein said microbicide is nonoxynol-9.

41. The barrier-forming composition as set forth in claim 37, wherein said microbicide is encapsulated in liposomes.

42. The barrier-forming composition as set forth in claim 38, wherein said microbicide is encapsulated in liposomes.

* * * * *